United States Patent
Hoff et al.

(10) Patent No.: US 8,235,966 B1
(45) Date of Patent: Aug. 7, 2012

(54) ELECTROMANIPULATION METHOD

(75) Inventors: Andrew M. Hoff, Tampa, FL (US);
Richard Gilbert, Tampa, FL (US);
Richard Heller, Norfolk, VA (US);
Mark J. Jaroszeski, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 199 days.

(21) Appl. No.: 12/848,703

(22) Filed: Aug. 2, 2010

Related U.S. Application Data

(60) Division of application No. 10/605,126, filed on Sep. 10, 2003, now Pat. No. 7,769,440, which is a continuation of application No. PCT/US02/07637, filed on Mar. 13, 2002.

(60) Provisional application No. 60/275,326, filed on Mar. 13, 2001.

(51) Int. Cl.
*A61M 31/00* (2006.01)
*A61N 1/30* (2006.01)
(52) U.S. Cl. .............. 604/501; 604/20; 607/3
(58) Field of Classification Search ............ 604/20, 604/501; 607/3
See application file for complete search history.

(56) References Cited

U.S. PATENT DOCUMENTS

| | | | |
|---|---|---|---|
| 3,571,629 A * | 3/1971 | Hilberman | 327/39 |
| 5,246,418 A * | 9/1993 | Haynes et al. | 604/20 |
| 5,298,017 A * | 3/1994 | Theeuwes et al. | 604/20 |
| 5,472,443 A * | 12/1995 | Cordis et al. | 606/48 |
| 5,551,953 A * | 9/1996 | Lattin et al. | 604/20 |
| 5,911,223 A * | 6/1999 | Weaver et al. | 128/898 |
| 5,983,131 A | 11/1999 | Weaver et al. | |
| 6,029,090 A * | 2/2000 | Herbst | 607/66 |
| 6,047,215 A * | 4/2000 | McClure et al. | 607/101 |
| 6,135,990 A | 10/2000 | Heller et al. | |
| 6,148,232 A * | 11/2000 | Avrahami | 604/20 |
| 6,295,469 B1 * | 9/2001 | Linkwitz et al. | 604/20 |
| 6,592,611 B1 * | 7/2003 | Zawada | 607/89 |
| 6,597,946 B2 * | 7/2003 | Avrahami et al. | 604/20 |
| 6,711,435 B2 * | 3/2004 | Avrahami | 604/20 |
| 6,738,663 B2 * | 5/2004 | Schroeppel et al. | 607/2 |
| 6,801,804 B2 * | 10/2004 | Miller et al. | 604/20 |
| 2002/0010414 A1 * | 1/2002 | Coston et al. | 604/20 |
| 2002/0038101 A1 * | 3/2002 | Avrahami et al. | 604/20 |
| 2003/0208235 A1 * | 11/2003 | Miller et al. | 607/3 |

* cited by examiner

*Primary Examiner* — Nicholas D Lucchesi
*Assistant Examiner* — Aarti Berdichevsky
(74) *Attorney, Agent, or Firm* — Molly L. Sauter; Smith & Hopen, P.A.

(57) ABSTRACT

The present invention is a method for electromanipulation of chemical species in vivo relative to a target tissue utilizing a nonconductive, conformable array base adapted to be placed coincident to the target tissue, a plurality of electrode elements projecting from the array base towards the target tissue, the electrode elements addressable individually, an electrical source coupled to the plurality of electrodes, a control means interposed between the electrical source and the plurality of electrode elements and in circuit communication therein, the control means adapted to establish an electrical potential between at least two electrodes, and a delivery means adapted to introduce chemical species to the target tissue.

5 Claims, 4 Drawing Sheets

ELECTROMANIPULATION METHOD

PRIORITY CLAIM

This application is a divisional of U.S. patent application Ser. No. 10/605,126 filed on Sep. 10, 2003 which was a continuation of International Application No. PCT/US2002/07637, filed on Mar. 13, 2002, which claims the benefit of U.S. Provisional Patent Application 60/275,326, filed Mar. 13, 2001, the contents of which are herein incorporated by reference.

FIELD OF INVENTION

This invention relates to devices and methods for delivering a molecule into a tissue, and more particularly in the field of electroporation and electromigration.

BACKGROUND OF THE INVENTION

The exposure of cells to intense electric fields for brief periods of time temporarily destabilizes membranes. This effect has been described as a dielectric breakdown due to an induced transmembrane potential, and was termed "electroporation", or "electropermeabilization", because it was observed that molecules that do not normally pass through the membrane gain intracellular access after the cells were treated with electric fields. The porated state was noted to be temporary. Typically, cells remain in a destabilized state on the order of minutes after electrical treatment ceases.

Various devices and methods for achieving electroporation have been described, including those of a subset of the present inventors (U.S. Pat. No. 6,135,990) and that of Weaver (U.S. Pat. No. 5,983,131).

Present devices and methods are relatively large-scale, occurring over centimeters, with electrodes placed in a fixed configuration. Two basic electrode types are currently known by those in the art. A first type comprises two flat parallel plates. A second type is formed of two insertable needles. Flat plates are limited in their use as little control over the depth of electric field penetration into tissue is achieved. The two-needle system is also limited as the total volume of tissue treatable with this type of array is limited to a narrow rectangle of tissue between the two needles. Furthermore, needle electrodes are adapted to deliver peak power in the kilowatt range across electrode pairs separated by relatively large distances.

Accordingly, what is needed in the art is an electroporation device that utilizes lower levels of activation energy to minimize tissue damage and patient discomfort.

There is another need in the art for an electroporation device that conforms to three-dimensional in vivo tissue structures.

There is another need in the art for an electroporation device able to perform electromigration of molecules wherein they are coincident to the target tissue.

It is, therefore, to the effective resolution of the aforementioned problems and shortcomings of the prior art that the present invention is directed.

However, in view of the prior art in at the time the present invention was made, it was not obvious to those of ordinary skill in the pertinent art how the identified needs could be fulfilled.

SUMMARY OF THE INVENTION

It is an object of the present invention to provide a device and method for achieving molecular delivery into a target tissue.

It is another object to provide such a device and method that facilitates electroporation with a lower applied power than those used in previously known techniques.

It is another object to provide such a device and method that facilitates electroporation with a lower applied voltage than those used in previously known techniques.

It is another object to provide such a device and method that incorporates a reservoir for supplying chemical species for molecular movement and/or delivery.

It is a further object to provide such a device and method that is conformable to a plurality of target tissues.

These and other objects are achieved with the present invention. The device comprises an array base having a substantially flexible distal face, the distal face adapted to be positioned adjacent a target tissue. A plurality of discrete electrodes are affixed in spaced relation about the array base. Each electrode is in circuit communication with a respective portion of a source of electrical energy and is so positioned with respect to the array base that it can establish an electric field in vivo between itself and other selected electrodes sufficient to cause transient permeability of a cell membrane within the target tissue.

The various embodiments of the device permits the user to employ a decreased excitation force to accomplish in vivo electroporation and/or electromigration. The plurality of electrodes and the programmability of their excitation pattern permits the user to control the density of interaction between the force and the target tissue. The flexibility of the array base's distal face provides an effective coupling to the target tissue, whether in a two- or three-dimensional configuration. Even tubular structures can be accommodated with an array base that can be wrapped around them or inserted inside them. In addition, volumetric covered surfaces can be created by wrapping an array base around the surface of an inflated or inflatable balloon like substrate.

The plurality of electrode elements as arranged within or on the array base are connected via wiring to accept anodic, cathodic, and/or ground signals such that electroporation can be effected by the electric field created by applied voltage waveforms as presented to the in vivo target tissue by these addressable array elements.

The present invention comprises a device for electromanipulation of chemical species in vivo relative to a target tissue. Electromanipulation should be construed to include both electroporation and electromigration. An array base adapted to be placed coincident to the target tissue is provided with a plurality of electrode elements secured in spaced art relation on the array base. The electrode elements comprise various anodes and cathodes on top of, or imbedded into the array base. The electrode elements may project from the array base towards the target tissue, or may be integral to the base. Preferably, the array base if formed of a nonconductive, conformable substrate adaptable to the topography of the tissue under in vivo treatment. Alternatively, the array base may be of substantially rigid construction provided it is formed with a geometric shape adapted to facilitate contact between the electrodes and a corresponding target tissue. An electrical source is coupled to the plurality of electrodes wherein the electrode elements, either individually, or as a group, are addressable by the electrical source. In a preferred embodiment of the invention, the electrode elements are spaced together in sufficient proximity to insure that that a peak power of less than 1 kilowatt is needed for electromanipulation of the target tissue. An embodiment of the invention may include an electrical source integral to the array base.

One or more fluid reservoirs adapted to deliver chemical species to the target tissue may be provided with at least one micro plunger. At least one porous electrode element capping the at least one micro plunger may also be provided whereby chemical species held with the at least one micro plunger are released through the at least one porous electrode element to the target tissue. Alternatively, at least one external reservoir adapted to hold chemical species may be provided and at least one conduit fluidly coupling the at least one reservoir to the array base established whereby the chemical species are delivered through the at least one conduit to the array base for delivery to the target tissue.

A thin film of chemical species on the array base may also be established whereby the chemical species are delivered to the target tissue when the array base is coincident to the target tissue. The chemical species may be retained within the thin film by absorption means and released from the thin film by application of an energy means including, but not limited to, voltaic, sonic or photonic sources. A control means is interposed between the electrical source and the plurality of electrode elements and in circuit communication therein, the control means is adapted to establish an electrical potential between at least two electrodes and a delivery means adapted to introduce chemical species to the target tissue.

In association with the novel device, a method of use for electromanipulation of chemical species in vivo relative to a target tissue includes the steps of placing at least one array base coincident to a target tissue, the at least one array base containing a plurality of electrode elements, establishing an electrical potential between at least two electrode elements in the plurality of electrode elements, providing a chemical species coincident to the target tissue, and controlling the electrical potential whereby the chemical species are delivered to the target tissue. The electrical potential may effect electromigration of the chemical species to the target tissue, the electroporation of the target tissue, or may effect both in substantially concurrent synchronization. A predetermined sequence of electrical potentials is established for the plurality of electrode elements and the predetermined sequence is then executed.

An alternative embodiment of the invention includes a method for combining at least two distinct of chemical species in vivo relative to a target tissue including the steps of placing at least one array base coincident to a target tissue, the at least one array base containing a plurality of electrode elements, establishing a first chemical staging location, establishing a second chemical staging location, establishing a chemical reaction location, introducing a first chemical species to the first chemical staging location, introducing a second chemical species to the second chemical staging location, establishing an electrical potential between at least two electrode elements in the plurality of electrode elements, and controlling the electrical potential to migrate the first and second chemical species towards the chemical reaction location. The electrical potential may effect an oxidation reaction on the first chemical species, the second chemical species, and/or a combination thereof. Once the first and second chemical species are moved to the chemical reaction location, they may be further electromigrated to the target tissue.

It is to be understood that both the foregoing general description and the following detailed description are explanatory and are not restrictive of the invention as claimed. The accompanying drawings, which are incorporated in and constitute part of the specification, illustrate embodiments of the present invention and together with the general description, serve to explain principles of the present invention.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
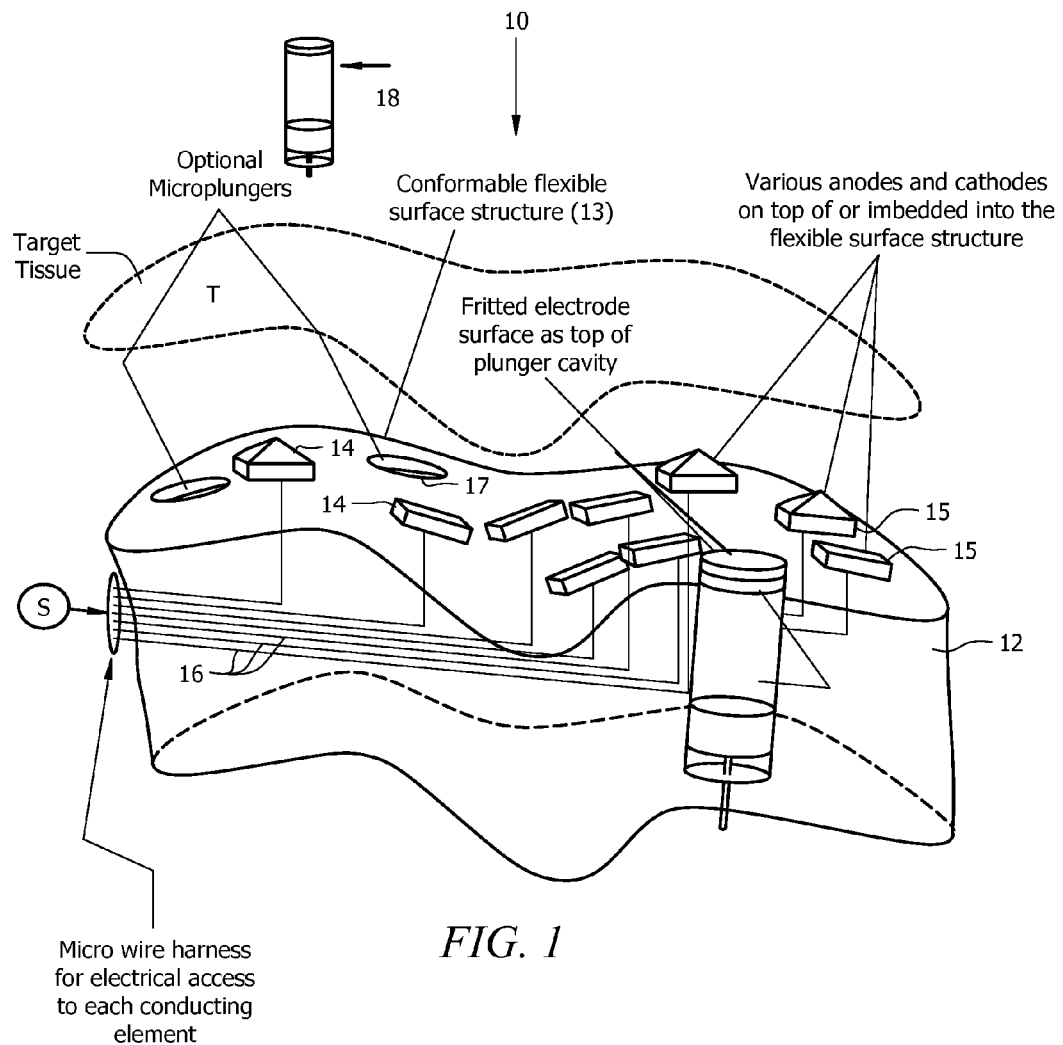
FIG. 1 is a diagrammatic view of the invention.
Figure 2:
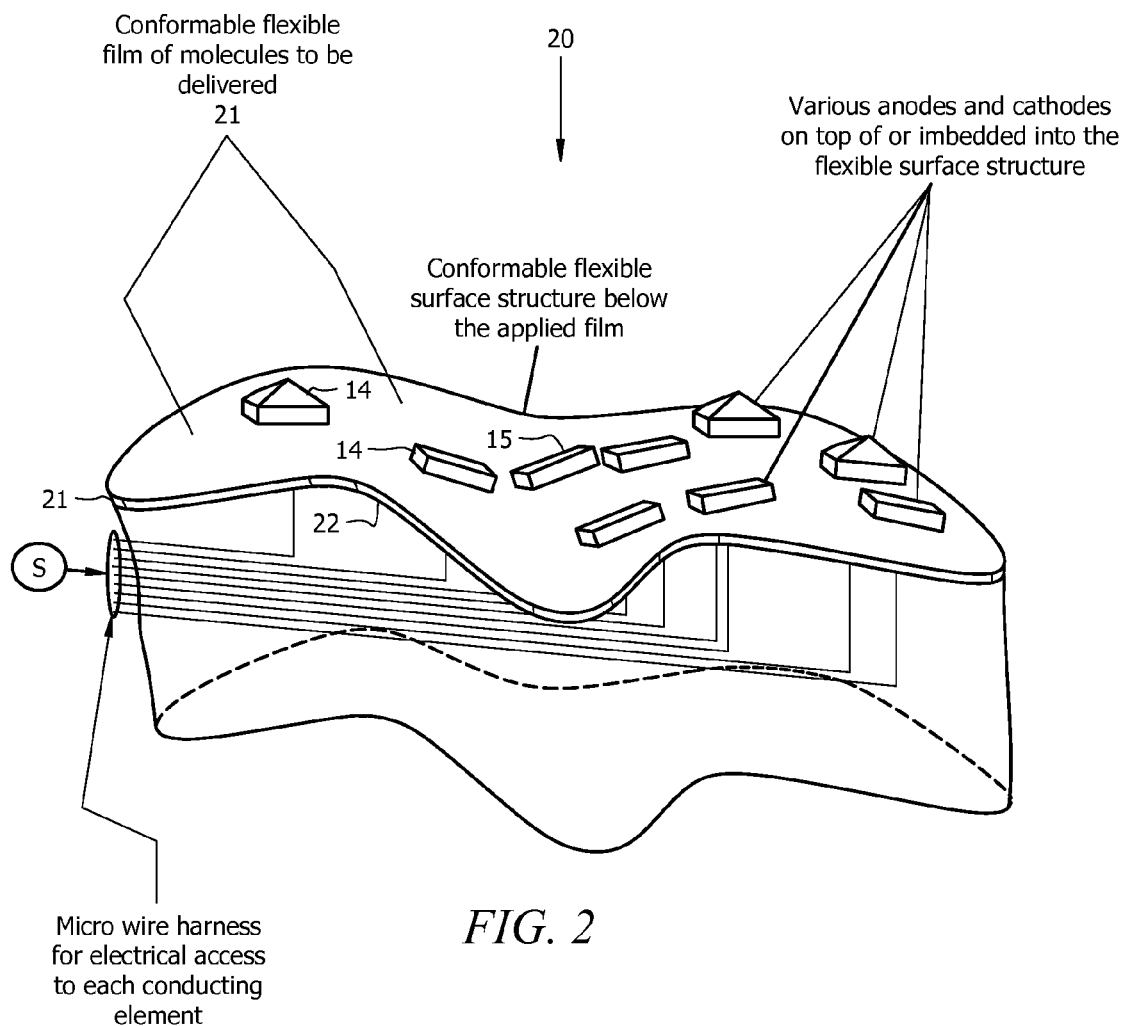
FIG. 2 is a diagrammatic view of an alternative embodiment of the invention employing a thin film of chemical species.
Figure 3:
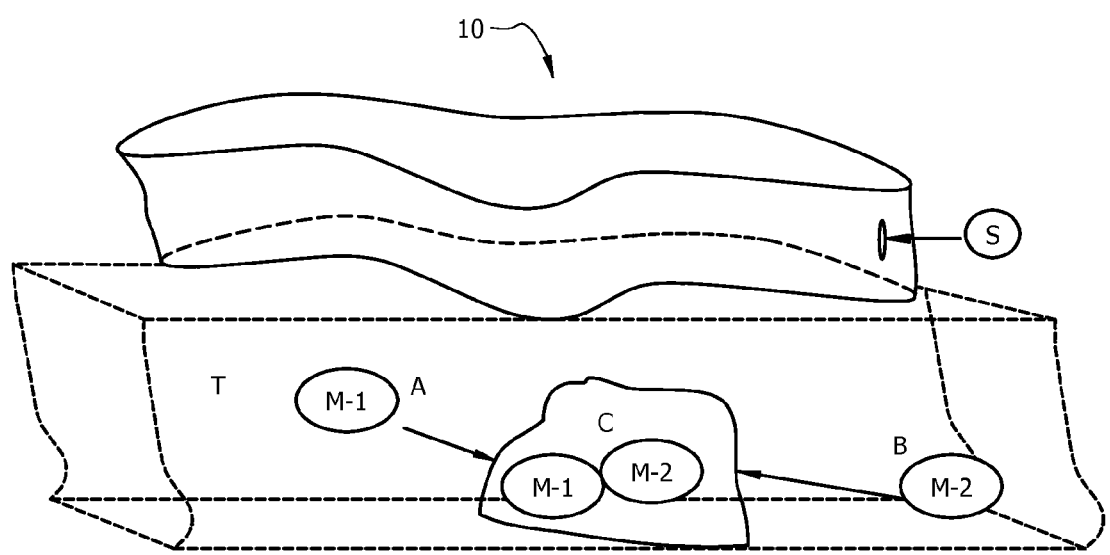
FIG. 3 is a diagrammatic view of a method of the invention for migrating at least two chemical species to a reaction location.

A description of the preferred embodiments of the present invention will now be presented with reference to FIGS. 1, 2, and 3.

A first embodiment of the device 10 (FIG. 1) comprises an array base 12 that has a flexible distal face 13 for conforming to a target tissue T. The target tissue may comprise, for example, skin, an internal organ, or a tumor. Affixed to the base 12 is a plurality of electrodes, comprising cathodes 14 and anodes 15, each having a distal portion protruding from the base 12 for contacting the tissue T. Each of the electrodes 14,15 is electrically coupled with a voltage and/or current source S by way of a conducting means 16. Preferably the source S comprises a programmable source so that a desired pattern of activation may be effected, such as, but not limited to, a D/A array (Analog Devices, Inc.), a commercially available power supply (WaveTek, HP, Tektronics, etc.), or a commercially available dedicated electroporation power supply (Genetronics, BioRad, etc.)

It will be appreciated by one of skill in the art that numerous arrangements of the electrodes 14,15 may be contemplated. For example, substantially flat electrodes may be affixed to the array base's distal face 13 as shown in FIG. 1. Alternatively, the electrodes 14,15 may be embedded in the array base 12 in a three-dimensional pattern, so long as the activating portion of the electrode is sufficiently close to the distal face 13 that an applied energy may penetrate to the target tissue T to perform a desired activation.

Since a multiplicity of electrode elements may be involved, electric fields are typically applied by electrodes in opposite groups of positive polarity (+) and negative polarity (−) in a manner that is approximately simultaneous. A group is a collection of one or more electrodes with each electrode in the group having substantially similar electrical potential at a time that is approximately simultaneous. In addition, electrodes can be activated in groups such that a group comprising (+) electrodes is opposite to an group comprising grounds and/or a group comprising (−) electrodes is opposite to a group comprising grounds. Combinations of these positive polarity, negative polarity, and/or ground groups are anticipated. For example, three groups of electrodes in an array might be connected such that, one group is (+), a second group is (−) and a third group is at ground potential. In addition, it is not necessary to have all three types of groups, (+), (−), and ground, active at any time; the minimum requirement is that any two types of groups must be active at approximately the same time.

If there are equal numbers of electrodes in each group, for example a group with at least one positive electrode opposed to a group containing an equal number of negative electrodes, thus defining an equal sum or what may be termed an "equal pair" situation. One example of an equal pair configuration might be a two group embodiment in which a group of 6 (+) electrodes opposed to a group containing 6 electrodes at ground potential. Other equal pair configurations between two groups are possible.

Combinations that do not represent equal pairs can may be envisioned by those of ordinary skill in the art. A first embodiment may include unequal sums of the electrodes in each group; e.g., 4 (+) electrodes are opposed to 3 (−) electrode, 3 (+) electrodes are opposed to 4 (−) electrodes, 7 (+) electrodes are opposed to 15 ground electrodes, and 2 (−) electrodes are opposite to 1 ground electrode. Thus, when the sum of the electrodes in each group are not equal they are considered to be defined as unequal pairs.

Furthermore, a configuration consisting of more than two opposing groups of electrodes is possible. For example, it may be desirable to selectively apply a different voltage with a predetermined pattern in a manner that is approximately simultaneous. Exemplary permutations may include a group of three electrodes with applied voltage, V-1, a group of four electrodes with an applied voltage V-2, and a group of two electrodes with an applied voltage, V-3, wherein the voltage values are substantially different. The definitions "equal pairs" and "unequal pairs" still apply. In this example, when more than two groups of electrodes are utilized, these definitions are simply extended so that if there is at least one group with a unique sum of electrodes the configuration is identified as an unequal pair situation.

It is further envisioned that the electrode elements can be addressed independently or in what is termed a set. A set is any collection of electrode elements that have the same address. An address for a set can be achieved either by applying the same address to independent electrode elements or by connecting separate electrode elements together so that they are all accessed by a single address signal.

Since a multiplicity of electrode elements 14,15 may be provided, limited only by geometric constraints, a precise tailoring of field patterns (pulse shape, height, strength, etc.) may be achieved, allowing an application of a desired electric field with accurate control of the applied voltage and/or current. The materials and flexible array base distal face 13 also permits a geometry that, allows a peak power less than 1 kW to be used to achieve electroporation. Such lower levels of activation energy minimize electrically induced tissue damage and may reduce or eliminate pain to the patient that can be associated with an electrical field.

It will also be appreciated by one of skill in the art that the array base 12 may take any of a number of configurations. An exemplary array base 12 comprises a substantially planar structure that may be laid upon a surface of a target tissue T. Another comprises a tape-like structure that may be placed in surrounding relation to a tube-like tissue T such as, but not limited to, a vessel, nerve, or gastrointestinal component. A third comprises an array structure that is wrapped around a balloon like substrate and inserted within the treatment tissue site so that the balloon and structure can expand and conform to the inner margin of the treatment site. It is also envisioned that the extent of expansion may vary with respect to treatment time and duration.

A particular arrangement comprises a ball grid array of electrodes mounted on a flexible polymer having a density of addressable cathodic or anodic elements of 125 □m (micrometer) in the X and Y axis, providing an array density of 64 elements per mm$^2$ The electrode elements 14,15 in a particular embodiment comprise a conductive material compatible with the intended in-vivo and or in-vitro application. Exemplary materials may include, but are not intended to be limited to, gold, titanium, titanium nitride, and a conductive polymer. The array base 12 may comprise a material such as KAPTON (MYLAR), paralyene, or a silicon-based material.

The device 10 may also be implanted in a tissue or body to permit repeated, programmed time or metabolic product release-driven responses. The device 10 may also be implanted with its own self-contained low power energy source. The electrode elements 14,15 may be adapted to emit photonic, sonic, and/or magnetic energy separately or in combination with electrical energy.

Energizing the electrode elements is achieved via conduits 16 that are coupled to individual electrode elements and are independently addressable in independent or aggregate relation. Desired conduit groupings are created by physical connections either interior or exterior to the device or by sending identical signals to specific groups of individually addressed conduits. The specific addressing of conduits or groups of conduits is accomplished by employing I/O software commands with the appropriate digital to analog interface devices or by the construction of a specific pattern of conductive contacts that can be engaged with the conduit pattern presented to the energy source S at the periphery of the device.

The device 10 may also comprise an element for introducing a desired substance into or adjacent the target tissue T. Such an element may comprise, for example, a micro plunger 17 having a lumen 18 through which a substance may be forced toward the base's distal face 13. A plurality of micro plungers may be provided, interspersed among the electrode elements 14,15. Alternatively, micro plungers 17 may be constructed with a porous electrode 19 that also serves as a lid on the distal end of the micro plunger cavity thus allowing fluid to pass to the treatment area.

Other embodiments include ball grid arrays affixed to a flexible tape that may be integrated into a catheter or other support structures. Ball grid arrays have a variety of ball densities and dimensions; thus, a variety of embodiments using various electrode configurations and electrode number densities is envisioned.

An additional embodiment of the device 20 (FIG. 2) a thin film 21 of the molecule desired to be delivered is applied to the base array's distal face 22. This permits the molecule to be positioned at the delivery site without the need for systemic or local introduction of the molecules by injection or other means.

A further embodiment of the device is a method for delivering one or more different chemical species (alternatively, different molecules or compounds developed from inorganic, organic, biochemical, in vitro, and/or in vivo synthesis) to a tissue T (FIGS. 1 and 2). This method comprises the steps of introducing a substance containing the molecule to an area in or adjacent to the target tissue T. A device such as device 10 is placed generally adjacent but in nonpenetrating fashion to a target tissue T, and electrode elements are used to apply electric fields to the tissue. The purpose of these applied fields is to cause electromigration of the desired molecules in the tissue; the purpose of these applied fields can also be to cause electroporation of the cells within the tissue. Fields that cause both electromigration and electroporation can be useful for distributing molecules within the tissue, permeabilizing the cell membranes, and moving molecules into permeabilized cells.

Yet another embodiment of this device (FIG. 3) is for bringing two types of molecules M-1 and M-2 into apposition within a target tissue T at a desired site C for permitting a reaction therebetween, as in multi component labile systems, or a "cell bomb". This method comprises the steps of introducing a substance containing a first molecule type M-1 into a first region adjacent the target tissue T and/or into a first region A within the target tissue T but adjacent to the desired target tissue site C and introducing a substance containing a second molecule M-2 into a second region adjacent the target tissue T and/or into a second region B within the target tissue T but adjacent the target tissue site C.

Next an electromigration of the first molecule M-1 and the second molecule M-2 is caused to a third region C within the target tissue T. The electromigration is caused by the application of energy from at least two electrode elements placed against a surface generally adjacent but in nonpenetrating fashion to a target tissue. The third region C may actually comprise the first region A or the second region B, or another region distinct therefrom. The first molecule M-1 and the second molecule M-2 are then permitted to react at the third region C.

It is also envisioned that there could be more than two types of molecules drawn into the desired region in the target tissue in the same time frame by the disclosed device. Thus, the various molecule types that enter the target tissue region may behave as precursors for a desired reaction, reactants, or molecules that facilitate the biological intended affect of the reaction products. Such facilitation includes but is not limited to reaction equilibrium shift and molecular transport agents as well as alteration of any reaction product to facilitate its entry into a desired biochemical pathway and cycle. Alterations of a reaction production may also be accomplished by the disclosed device moving molecules into the target tissue T or target tissue site C some time or times after the desired reaction at site C has occurred. The timing and movement of such molecules accomplished by the disclosed device is dependent on the desired interaction with the pathway or cycle in question.

Numerous other ways of practicing the invention described in this application are possible. These include, but are not limited to using the described devices to cause: (1) electromigration, electroporation, and then electromigration again; (2) electromigration, followed by electroporation; (3) electroporation, followed by electromigration; (4) electroporation alone; (5) electromigration alone; (6) electromigration from a plurality of sides, either alone or (7) in combination with electroporation, either (8) before the electromigration or (9) after the electromigration or (10) simultaneously.

In addition, by using the instant devices as described above it is possible to perform electromigration as well as electroporation using the same electrodes or, alternately, different electrodes. As known by those of ordinary skill in the art, the magnitude and duration of the electric fields required to achieve the desired effect is dependent on the particular combination of molecule and tissue under investigation; therefore, the electric field magnitudes and durations may be equal or variable for inducing the migration of molecules and the electroporation of cells within tissues.

It may be appreciated by one skilled in the art that additional embodiments may be contemplated, including different electrode configurations adapted to provide high and low level fields for causing electromanipulation. A device configured to produce an electromagnetic field in vivo preferably has the following properties (1) the portion of the device that comes in contact with body tissue or fluid is made of biocompatible materials; (2) the electrodes are capable delivering the power required for electromanipulation of living cells in vivo in an electrolyte which may include the tissue being treated, interstitial fluid, injected material at the treatment site, material applied to the target tissue, and combinations of the foregoing, and (3) the material between the electrodes will have a sufficient dielectric constant so that it does not break down as a result of nearby electrodes possessing opposite polarity during electrical treatment. Moreover, it will be apparent to those skilled in the art that where an electrode or system is configured to perform both electromigration and electroporation, such an electrode or system may be used to perform either or both functions.

Figure 4:
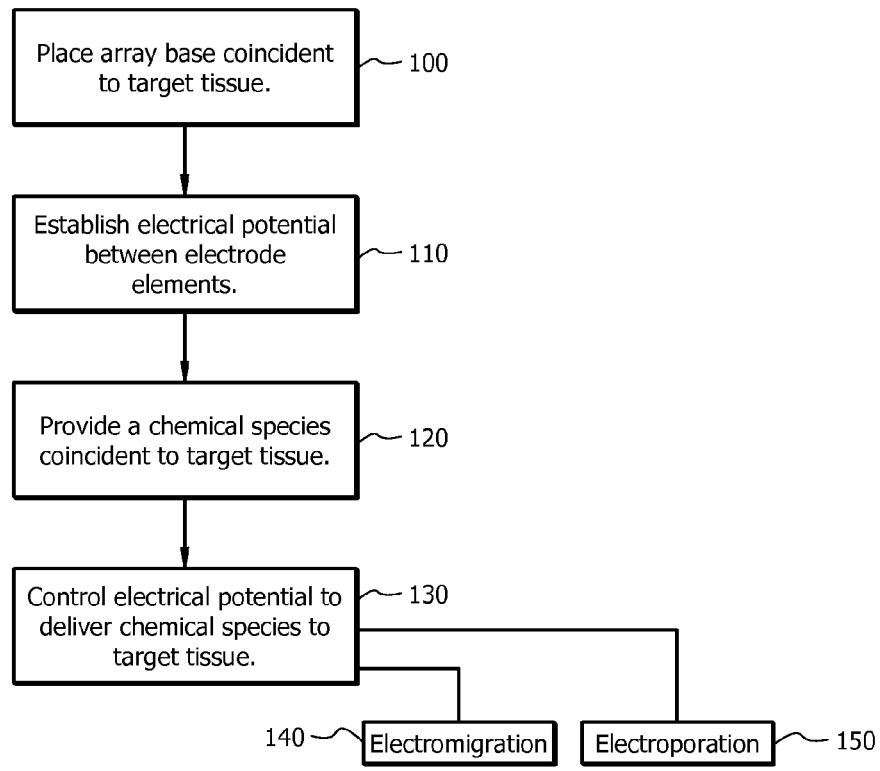
FIG. 4 is a diagrammatic view of the general method of the invention.
Figure 5:
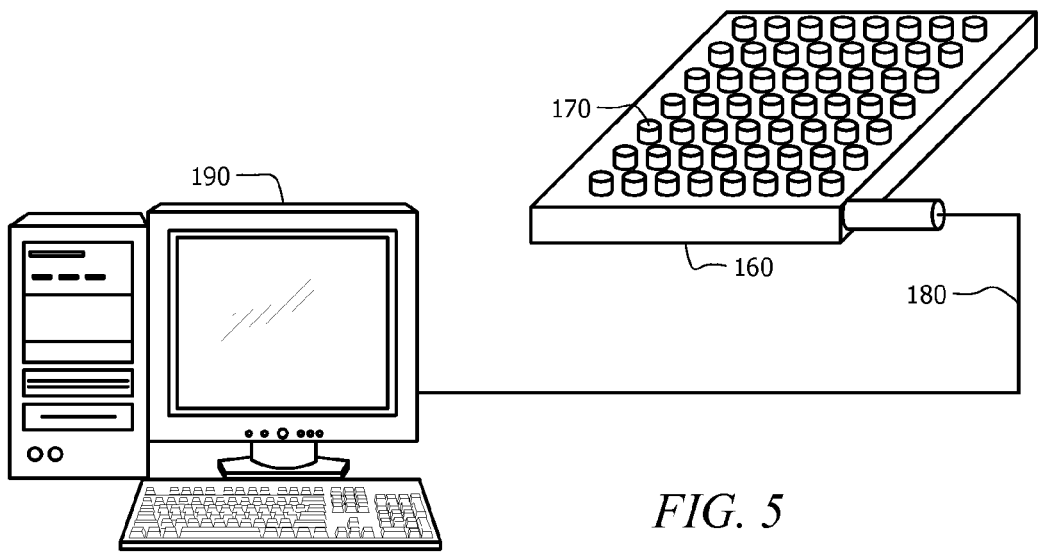
FIG. 5 is a diagrammatic view of an alternative embodiment of the invention.

In FIG. 4, an array base is placed coincident to the target tissue 100. An electrical potential is established between electrode elements 110 and a chemical species is provided coincident to the target tissue 120. The electrical potential of the electrode elements is controlled to deliver the chemical species to the target tissue 130 by electromigration 140, electroporation 150 or a combination thereof. FIG. 5 illustrates a microelectrode 160 formed of a plurality of discrete electrodes 170 comprising the array. A microwire 180 circuitly coupled to each discrete electrode 170 is coupled to a computing means 190. The computing means is preferably a personal computer configured with an A/D input/output card. The microelectrode 160 may be placed on the tip of tweezer-type instruments wherein highly precise electromigration and/or electroporation may be achieved in vivo.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for combining at least two distinct chemical species in vivo relative to a target tissue comprising the steps of:

placing at least one substantially planar nonconductive sheet conformable to the three-dimensional topography of the surface of the target tissue coincident to the target tissue, the at least one sheet containing a plurality of independently addressable electrode elements;

establishing a first chemical staging location;

establishing a second chemical staging location;

establishing a chemical reaction location;

introducing a first chemical species to the first chemical staging location;

introducing a second chemical species to the second chemical staging location;

applying a controlled voltage between at least three independently addressable electrode elements of the plurality of electrode elements and controlling the current drawn by the electrode elements as a result of the applied voltage to insure that a peak power of less than about 1 kilowatt is delivered to the target tissue;

controlling the electrical potential to migrate the first and second chemical species towards the chemical reaction location.

2. The method of claim 1, wherein the electrical potential effects an oxidation reaction on the first chemical species.

3. The method of claim 1, wherein the electrical potential effects an oxidation reaction on the second chemical species.

4. The method of claim 1, wherein the electrical potential effects an oxidation reaction on a combination of the first and second chemical species.

5. The method of claim 1, further comprising the step of electromigrating a combination of the first and second chemical species from the chemical reaction location to the target tissue.

* * * * *